United States Patent [19]

Costerousse et al.

[11] 4,257,948
[45] Mar. 24, 1981

[54] NOVEL EPOXIDATION AGENT AND PROCESS

[75] Inventors: Germain Costerousse, Saint-Maurice; Jean G. Teutsch, Pantin, both of France

[73] Assignee: Roussel Uclaf, Paris, France

[21] Appl. No.: 29,135

[22] Filed: Apr. 11, 1979

[30] Foreign Application Priority Data

Apr. 19, 1978 [FR] France ................................ 78 11517

[51] Int. Cl.$^3$ .............................................. C07J 17/00
[52] U.S. Cl. ............................. 260/239.55 R; 568/419
[58] Field of Search .................. 260/239.55 R, 593 H

[56] References Cited

FOREIGN PATENT DOCUMENTS 2149428  3/1973  France ................................ 260/239.55

Primary Examiner—Elbert L. Roberts
Attorney, Agent, or Firm—Hammond & Littell, Weissenberger and Muserlian

[57] ABSTRACT

A novel epoxidation agent comprising hydrogen peroxide and hexachloroacetone and a novel process for epoxidizing an acyclic, cyclic or polycyclic compound containing at least one ethylenic unsaturation.

12 Claims, No Drawings

NOVEL EPOXIDATION AGENT AND PROCESS

STATE OF THE ART

A number of epoxidation agents are known such as concentrated hydrogen peroxide in an alkaline solution and peracids such as peracetic acid, perphthalic acid and m-chloroperbenzoic acid. It is also known from French Pat. Nos. 2,201,187 and 2,149,428 that hydroperoxide of hexafluoroacetone and hydrogen peroxide in the presence of the hexafluoroacetone which are excellent laboratory reagents for epoxidation and the hydroperoxide of hexafluoroacetone especially permits very specific reactions. However, the said reagents are extremely costly and hexafluoroacetone is, in effect, a very dear product and besides, it has practically disappeared from the market place so that it is mainly sold in the form of its sesquihydrate. The hydroperoxide of hexafluoroacetone prepared from the perhydrol and hexafluoroacetone is also a very dear product and for these reasons, neither hydrogen peroxide in the presence of hexafluoroacetone nor the hydroperoxide of hexafluoroacetone is a useful reactant on the industrial scale since, for example, it requires 1 to 2 moles of the hydroperoxide of hexafluoroacetone per mole of the compound to be expodized to obtain good yields.

OBJECTS OF THE INVENTION

It is an object of the invention to provide a novel epoxidized agent consisting essentially of hydrogen peroxide in the presence of hexachloroacetone which is a more specific reactant which may be used in a neutral medium.

It is another object of the invention to provide a novel process for epoxidizing compounds containing at least one epoxidizable ethylenic unsaturation.

These and other objects and advantages of the invention will become obvious from the following detailed description.

THE INVENTION

The novel epoxidation agent of the invention is comprised of hydrogen peroxide in the presence of hexachloroacetone which is useful on the industrial scale since it is a cheap reactant which gives a very selective epoxidation reaction in excellent yields. As well as being a cheap reactant, it is not necessary to use large amounts of hexachloroacetone as catalytic quantities are sufficient.

For catalytic quantities of hexachloroacetone, it is meant that molar amounts of hexachloroacetone less than one fourth the molar amounts of the compounds to be epoxidized are used. It is possible to obtain very good epoxidation yields when using low amounts of hexachloroacetone. Excellent epoxidation yields in the epoxidation of steroids may be obtained with 0.2 or 0.1 moles of hexachloroacetone per mole of steroid to be epoxidized.

French Pat. No. 2,201,187, as noted above, describes the use of the hydroperoxide of hexafluoroacetone for the epoxidation of unsaturated organic compounds which is prepared by bubbling hexafluoroacetone into a concentrated hydrogen peroxide solution and equimolar amounts of hexafluoroacetone and hydrogen peroxide are required. The said French patent also teaches that the preferred mode of the process requires 1 to 2 moles of the hydroperoxide of hexafluoroacetone per mole of compound to be epoxidized.

It is unexpected that the reactant of the invention which is hydrogen peroxide in the presence of hexachloroacetone only requires catalytic amounts of hexachloroacetone. One would expect that equimolar amounts of hydrogen peroxide, hexachloroacetone and the compounds to be epoxidized would have to be used but it has been very clearly found that excellent epoxidation yields are obtained using only catalytic amounts of hexachloroacetone. Preferably the epoxidation reagent consists of hydrogen peroxide in the presence of a catalytic amount of hexachloroacetone which is to be hydrogen peroxide containing 1 to 20 mole percent of hexachloroacetone, and preferably 5 to 15 mole percent of hexachloroacetone.

The reactant of the invention also has the advantage of very selective reactions with excellent yields and especially permits selective epoxidation in very good yields of a single double bond in a compound containing more than one double bond. For example, $\Delta^{5(10),9(11)}$-estradienes may be epoxidized to obtain only a 5(10)-epoxy group with almost quantitative yields while with the usual epoxidation reagents such as M-chloroperbenzoic acid, a mixture of 5(10)-epoxy and 9(11)-epoxy derivatives is obtained [Nedellec, Bull. Soc. Chim., Vol. 70 No. 7 p. 2548].

The novel process of the invention comprises reacting an acyclic, cyclic or polycyclic compound containing at least one ethylenic unsaturation with an epoxidation agent comprising hydrogen peroxide in the presence of a catalytic amount of hexachloroacetone to form the corresponding epoxidized compound which may be recovered. The reaction is preferably effected at $-10°$ to $30°$ C., especially $-5°$ to $+5°$ C. in a chlorinated organic solvent such as methylene chloride or chloroform and optionally in the presence of a tertiary base such as pyridine.

The compound to be epoxidized may be a linear compound containing an ethylenic double bond such as ethylene or a monocyclic compound, especially those with 5,6 or 7 chain components containing an ethylenic double bond such as cyclohexene or terpenic derivatives.

Examples of suitable polycyclic compounds containing at least one ethylenic double bond are steroids which are the preferred reactants of the invention to be epoxidized. Preferred steroids are those containing a 3-ketal group and a double bond in the $\Delta^{5(6)}$-position to form the corresponding 3-ketal-5,6-epoxy-steroid as a mixture of $5\alpha,6\alpha$-epoxy and $5\beta,6\beta$-epoxy isomers which may be separated as individual isomers by known methods, if desired. Known methods of separating such isomers include selective crystallization and chromatography.

The process of the invention is also useful with steroids containing a 3-ketal group and ethylenic double bond in the $\Delta^{5(10)}$ and $\Delta^{9(11)}$-positions to obtain the corresponding 3-ketal-5,10-epoxy-$\Delta^{9(11)}$ steroid as a mixture of the $5\alpha,10\alpha$-epoxy and $5\beta,10\beta$-epoxy isomers which may be separated, if desired. The starting steroid may also have a 3-lower alkoxy group and double bonds in the $\Delta^{5(10)}$ and $\Delta^{9(11)}$-positions to obtain the corresponding 3-alkoxy-5,10-epoxy-$\Delta^{9(11)}$-steroid as a mixture of the $5\alpha,10\alpha$-epoxy and $5\beta,10\beta$-epoxy isomers which may be separated.

In the following examples there are described several preferred examples to illustrate the invention. However, it is to be understood that the invention is not intended to be limited to the preferred embodiments.

EXAMPLE 1

17,20,20,21-bis-(methylenedioxy)-5α,6α-epoxy-3,3-ethylene-dioxy-16α-methyl-pregnane-11-one A solution of 1.5 g of 17,20,20,21-bis-(methylenedioxy)-3,3-ethyenedioxy-16α-methyl-Δ$^5$-pregnene-11-one in 9 ml of methylene chloride under a nitrogen atmosphere was cooled to 0° C. and then 0.06 ml of hexachloroacetone followed by 0.15 ml of 85% hydrogenperoxide were added thereto. The mixture was stirred at 20° C. under nitrogen for 72 hours and after the addition of another 0.06 ml of hexachloroacetone, the mixture was stirred for another 24 hours. The mixture was poured into a solution of 30 ml of 0.5 M sodium thiosulfate and 20 g of ice and the mixture was extracted with methylene chloride. The organic phase was washed with water and dried over sodium sulfate to obtain 1.7 g of a product which was empasted with isopropyl ether and dried to obtain 1.24 g of 17,20,20,21-bis-(methylenedioxy)-5α,6α-epoxy-3,3-ethylenedioxy-16α-methyl-pregnane-11-one melting at 248° C. RMN Spectrum (deuterochloroform): H$_6$ at 169–172.5 Hz.

EXAMPLE 2

3,3-20,20-bis-(ethylenedioxy)-5α,10α-epoxy-16α-methyl-19-nor-Δ$^{9(11)}$-pregnane A solution of 2 g of 3,3-20,20-bis-(ethylenedioxy)-16α-methyl-19-nor-Δ$^{5(10),9(11)}$-pregnadiene in 9 ml of methylene chloride containing a trace of pyridine was cooled to 0° C. and 0.075 ml of hexachloroacetone and then 0.82 ml of 30% hydrogen peroxide were added thereto with stirring. The mixture was stirred at 0° C. for 24 hours and was then poured into an iced solution of sodium thiosulfate containing a trace of pyridine. The mixture was extracted with methylene chloride and the organic phase was washed with aqueous sodium thiosulfate, dried and evaporated to dryness to obtain 2.1 g of 3,3-20,20-bis-(ethylenedioxy)-5α,10α-epoxy-16α-methyl-19-nor-Δ$^{9(11)}$-pregnene.

RMN Spectrum (deuterochloroform): peaks at 1.04 to 1.12 ppm (16α-methyl); at 1.32 ppm (21-methyl); at 3.9 ppm (ketals); at 5.77 and 5.94 ppm (11-hydrogen).

EXAMPLE 3

3,3-dimethoxy-5α,10α-epoxy-Δ$^{9(11)}$-estrene-17-one 10.5 ml of hexachloroacetone and then 55 ml of 50% hydrogen peroxide were added to a solution of 210 g of 3,3-dimethoxy-Δ$^{5(10),9(11)}$-estradiene-17-one in 1050 ml of methylene chloride containing 1 ml of pyridine and the mixture was stirred at 16° C. for 24 hours and was then poured into an aqueous sodium thiosulfate solution. The mixture was extracted with methylene chloride and the organic phase was washed with water, dried and evaporated to dryness to obtain 246 g of 3,3-dimethoxy-5α,10α-epoxy-Δ$^{9(11)}$-estrene-17-one.

Various modifications of the compositions and process of the invention may be made without departing from the spirit or scope thereof and it should be understood that the invention is intended to be limited only as defined in the appended claims.

We claim:

1. An epoxidation agent comprising hydrogen peroxide and hexachloroacetone.

2. The agent of claim 1 containing a catalytic amount of hexachloroacetone.

3. In the process of reacting an acrylic, cyclic or polycyclic compound containing at least one ethylenic unsaturation with an epoxidation agent to obtain the corresponding epoxidized compound, the improvement comprising using as the epoxidation agent the composition of claim 1.

4. The process of claim 3 wherein a steroid containing at least one ethylenic unsaturation is reacted to obtain the corresponding epoxy steroid.

5. The process of claim 4 wherein the steroid has a 3-ketal group and a Δ$^{5(6)}$-double bond to obtain the corresponding 3-ketal-5,6-epoxy steroid as a mixture of 5α,6α-epoxy and 5β,6β-epoxy isomers which may be separated.

6. The process of claim 4 wherein the steroid has a 3-ketal group and double bonds on the Δ$^{5(10)}$ and Δ$^{9(11)}$-positions to obtain the corresponding 3-ketal-5,10-epoxy-Δ$^{9(11)}$-steroid as a mixture of the 5α,10α-epoxy and 5β,10β-epoxy isomers which may be separated.

7. The process of claim 4 wherein the steroid has a 3-alkoxy group and double bonds in the Δ$^{5(10)}$ and Δ$^{9(11)}$-positions to obtain the corresponding 3-alkoxy-5,10-epoxy-Δ$^{9(11)}$-steroid as a mixture of 5α,10α-epoxy and 5β,10β-epoxy isomers which may be separated.

8. The process of claim 3 wherein the reaction is effected at a temperature of −10° to 30° C.

9. The process of claim 8 wherein the temperature is −5° to +5° C.

10. The process of claim 3 wherein the reaction is effected in a chlorinated organic solvent.

11. The agent of claim 1 comprising hydrogen peroxide and 1 to 20 mole percent of hexachloroacetone.

12. The process of claim 3 wherein the agent contains 1 to 20 mole percent of hexachloroacetone based on the amount of hydrogen peroxide.

* * * * *